United States Patent
Nagai et al.

(10) Patent No.: US 11,441,115 B2
(45) Date of Patent: Sep. 13, 2022

(54) CELL CULTURE DEVICE

(71) Applicants: DAI NIPPON PRINTING CO., LTD., Tokyo (JP); OSAKA UNIVERSITY, Suita (JP); TERUMO KABUSHIKI KAISHA, Tokyo (JP)

(72) Inventors: Taro Nagai, Tokyo (JP); Yoshiki Sawa, Osaka (JP); Shigeru Miyagawa, Osaka (JP); Kenji Oyama, Kanagawa (JP)

(73) Assignees: DAI NIPPON PRINTING CO., LTD., Tokyo (JP); OSAKA UNIVERSITY, Suita (JP); TERUMO KABUSHIKI KAISHA, Tokyo (JP)

( * ) Notice: Subject to any disclaimer, the term of this patent is extended or adjusted under 35 U.S.C. 154(b) by 71 days.

(21) Appl. No.: 17/042,301

(22) PCT Filed: Mar. 12, 2019

(86) PCT No.: PCT/JP2019/009908
§ 371 (c)(1),
(2) Date: Sep. 28, 2020

(87) PCT Pub. No.: WO2019/188239
PCT Pub. Date: Oct. 3, 2019

(65) Prior Publication Data
US 2021/0009934 A1    Jan. 14, 2021

(30) Foreign Application Priority Data

Mar. 29, 2018    (JP) .............................. JP2018-063958

(51) Int. Cl.
*C12M 1/00*    (2006.01)
*C12M 1/22*    (2006.01)
(Continued)

(52) U.S. Cl.
CPC .............. *C12M 41/14* (2013.01); *C12M 1/22* (2013.01); *C12M 1/34* (2013.01); *C12M 1/38* (2013.01);
(Continued)

(58) Field of Classification Search
CPC ...................................................... C12M 41/14
See application file for complete search history.

(56) References Cited

U.S. PATENT DOCUMENTS

| 2005/0084420 A1* | 4/2005 | Osawa | ................... C12M 41/14 435/303.1 |
| 2020/0124836 A1* | 4/2020 | Miyoshi | ................. C12M 41/36 |

FOREIGN PATENT DOCUMENTS

| CN | 108300663 A | * | 7/2018 | .............. B01L 3/545 |
| JP | 2009-131275 A | | 6/2009 | |

(Continued)

OTHER PUBLICATIONS

Apr. 9, 2019 International Search Report issued in International Patent Application No. PCT/JP2019/009908.

*Primary Examiner* — Jonathan M Hurst
(74) *Attorney, Agent, or Firm* — Oliff PLC

(57) ABSTRACT

When detachment of a cell sheet from a culture dish has started at an unintended timing, immediately detach the cell sheet from the culture dish while preventing generation of wrinkles and the like in the cell sheet. A cell culture device captures an image of cells in the culture dish, and controls a cooling mechanism and a shaking mechanism based on the image so as to shake the cells while cooling them.

7 Claims, 2 Drawing Sheets

(51) Int. Cl.
*C12M 1/34* (2006.01)
*C12M 1/38* (2006.01)
*C12M 3/00* (2006.01)
*C12M 3/06* (2006.01)
*C12M 1/02* (2006.01)
*C12M 1/36* (2006.01)

(52) U.S. Cl.
CPC ............ *C12M 23/48* (2013.01); *C12M 27/16* (2013.01); *C12M 41/24* (2013.01); *C12M 41/48* (2013.01)

(56) References Cited

FOREIGN PATENT DOCUMENTS

| | | | |
|---|---|---|---|
| JP | 2011-115080 A | 6/2011 | |
| JP | 2012-152189 A | 8/2012 | |
| JP | 2013-192544 A | 9/2013 | |
| JP | 2016-052269 A | 4/2016 | |
| WO | WO-2013181713 A1 * | 12/2013 | ............ A61K 47/32 |

* cited by examiner

CELL CULTURE DEVICE

TECHNICAL FIELD

The present disclosure relates to devices for culturing cells.

DESCRIPTION OF THE RELATED ART

In the field of regenerative medicine, a method of implanting a cell sheet, which has been obtained by culturing cells in a sheet form, into a patient is known. To form a cell sheet, there is known a method of culturing cells on a culture dish whose adhesiveness to cells changes depending on temperature, for example. When such a method is used, there is a possibility that the cell sheet may become accidentally detached from the culture dish during the cultivation process.

Patent Literature 1 below discloses a technique of culturing a cell sheet. Specifically, Patent Literature 1 discloses a technique of, "with an objective of providing a system capable of easily detaching sheet-like cultured cells with even low strength from a culture vessel while reducing danger, such as wrinkles, breaks, damages, and contamination," "providing a system including (i) a housing unit that houses a culture vessel for culturing sheet-like cells, (ii) a shaking unit that shakes the culture vessel in the housing unit to detach the sheet-like cultured cells therefrom, (iii) a sensor unit that measures the initial state and the post-shake state of the sheet-like cultured cells in the culture vessel, and (iv) an analyzing unit that analyzes the state of the sheet-like cultured cells as a detached state when the difference between the values of the initial state and the post-shake state measured by the sensor unit is greater than a preset value, thereby achieving the objective." (See the abstract.)

CITATION LIST

Patent Literature

Patent Literature 1: JP 2011-115080 A

SUMMARY

If the cultivation is carried on without the operator noticing that the cell sheet has been detached from the culture vessel, adhesion between the cells is formed with the cell sheet in a bent state, causing the result that wrinkles may be generated in the sheet or the edge of the sheet may bulge. This results in degraded appearance of the cell sheet.

In the technique disclosed in Patent Literature 1, the culture vessel is shaken to allow the cell sheet to be detached therefrom without wrinkles or damages generated in the cell sheet. However, there is a possibility that the detachment of the cell sheet may occur at an unintended timing. The technique disclosed in Patent Literature 1 is intended to reliably detach the cell sheet at an intended timing but does not necessarily consider in detail how to address the detachment that may occur at an unintended timing.

The present disclosure has been made in view of the foregoing problem, and it is an objective of the present disclosure to, when detachment of a cell sheet from a culture dish has started at an unintended timing, immediately detach the cell sheet from the culture dish while preventing generation of wrinkles and the like in the cell sheet.

A cell culture device according to the present disclosure captures an image of cells in a culture dish, and controls a cooling mechanism and a shaking mechanism based on the image so as to shake the cells while cooling them.

According to the cell culture device of the present disclosure, detachment of a cell sheet from a culture dish at an unintended timing is detected from an image. Thus, it is possible to immediately detach the cells from the culture dish by shaking them while suppressing contraction of the cells by cooling them.

DESCRIPTION OF THE EMBODIMENTS

Embodiment 1: Device Configuration

Figure 1:
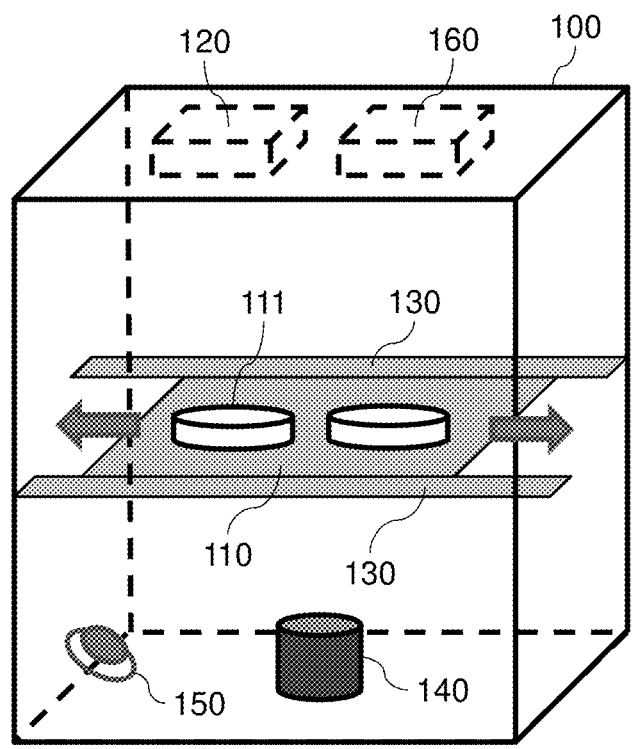
FIG. 1 is a configuration view of a cell culture device 100 according to Embodiment 1.

FIG. 1 is a configuration view of a cell culture device 100 according to Embodiment 1 of the present disclosure. The cell culture device 100 is a device for culturing cells by placing a cell sheet on a culture dish 111. The cell culture device 100 includes a plate 110, a cooling mechanism 120, a shaking mechanism 130, an imaging unit 140, a light 150, and a controller 160.

The plate 110 is a plate-like member on which the culture dish 111 is adapted to be placed. The cooling mechanism 120 is a device that cools cells on the culture dish 111 by cooling the internal space of the cell culture device 100, for example. The shaking mechanism 130 is a device that shakes the cells on the culture dish 111 by shaking the plate 110. The direction of shaking may be any of the horizontal direction, perpendicular direction, and a combination thereof. The imaging unit 140 captures an image of the cells on the culture dish 111 from below the plate 110. The light 150 illuminates a space around the region to be imaged by the imaging unit 140. The controller 160 controls the cooling mechanism 120 and the shaking mechanism 130 according to the image captured by the imaging unit 140.

In the process of culturing cells, there may be a case where the cells become detached from the culture dish 111 accidentally. In such a case, if the cultivation of the cells is continued, the cells will be cultured with the cell sheet in a bent state. Thus, wrinkles may be generated in the cell sheet or the edge of the cell sheet may bulge. This results in degraded appearance of the cell sheet. Thus, in Embodiment 1, accidental detachment of the cells is detected first.

The imaging unit 140 captures images of the cells, and the controller 160 periodically acquires the images at predetermined time intervals, for example. The controller 160 analyzes the images using an appropriate analysis method to detect whether the cells have been detached from the culture dish 111. If at least some of the cells have been detached from the culture dish 111, the controller 160 performs the procedures described below to prevent generation of wrinkles and the like in the cell sheet.

Embodiment 1: Operation Procedures

The controller 160, upon detecting from the cell images that detachment of the cells from the culture dish 111 has started, operates the cooling mechanism 120 to cool the cells and also operates the shaking mechanism 130 to shake the culture dish 111, thereby promoting the detachment of the cell sheet from the culture dish 111. The duration for operating the shaking mechanism 130 may be a duration until the cells are evaluated as completely detached based on the cell images captured by the imaging unit 140, or may be a predetermined period of time.

The cooling mechanism 120 cools the cells down to a temperature lower than the culture temperature for the cells. The culture temperature for the cells is typically 37° C. Thus, the cells are desirably cooled down to a temperature lower than that. Accordingly, it is possible to suppress the formation of adhesion between the cells, which would otherwise occur if the cultivation of the cells is continued in a bent state.

A combined use of the cooling mechanism 120 and the shaking mechanism 130 can suppress the formation of adhesion between the cells and thus can suppress the degraded appearance of the cell sheet, and can also perform a step of detaching the cells from the culture dish 111 concurrently. Accordingly, a high-quality cell sheet can be obtained while the operation efficiency of the cultivation step is also increased.

When a temperature-responsive vessel is used for the culture dish 111, the advantageous effects of the present disclosure can be further increased. Specifically, for example, it is considered that when the temperature of the culture dish 111 becomes lower than a threshold temperature, the adhesiveness of the culture dish 111 to the cells becomes sufficiently low, thus allowing the cells to be detached from the culture dish 111. Accordingly, when the cells are cooled by the cooling mechanism 120, the culture dish 111 is concurrently cooled, which can enhance the effect of detaching the cells. That is, the step of detaching the cells is allowed to proceed further efficiently. The response temperature of the culture dish 111 need not be necessarily equal to the cooling temperature of the cooling mechanism 120.

Figure 2:
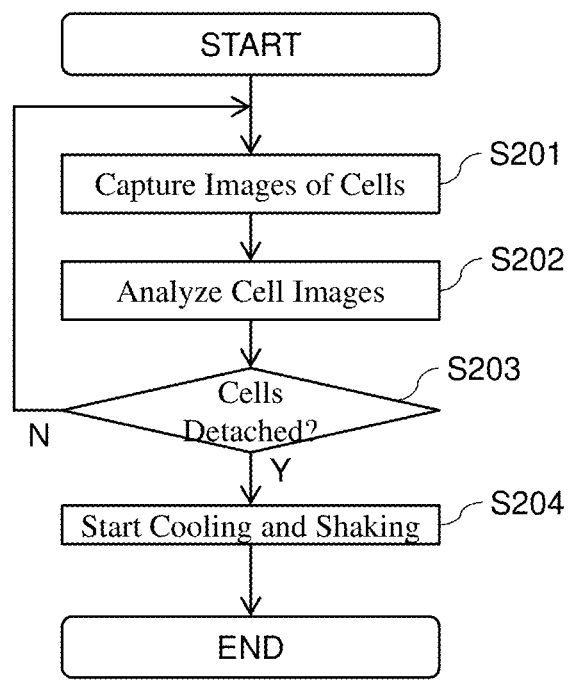
FIG. 2 is a flowchart illustrating the operation procedures of the cell culture device 100.

FIG. 2 is a flowchart illustrating the operation procedures of the cell culture device 100. The cell culture device 100 can execute this flowchart at predetermined time intervals, for example. Hereinafter, each step of FIG. 2 will be described.

The imaging unit 140 continuously captures images of the cells on the culture dish 111, and outputs the resulting image data to the controller 160 (S201). The controller 160 analyzes the image data on the cells (S202) and determines if detachment of the cells from the culture dish 111 has started (S203). If detachment of the cells is determined to have started, the cells are cooled by the cooling mechanism 120 and are also shaken by the shaking mechanism 130 (S204). If detachment of the cells is not determined to have started, the process returns to step S201.

Embodiment 1: Conclusion

The cell culture device 100 according to Embodiment 1, upon confirming that detachment of cells from the culture dish 111 has started, starts to cool the cells and also shakes them. Cooling the cells can suppress unintended formation of adhesion between the cells, which would otherwise occur if the cultivation of the cells is continued. In addition, shaking the cells concurrently with cooling can reliably detach the cell sheet from the culture dish 111 while suppressing failures, such as a bend of the cell sheet.

Embodiment 2

Figure 3:
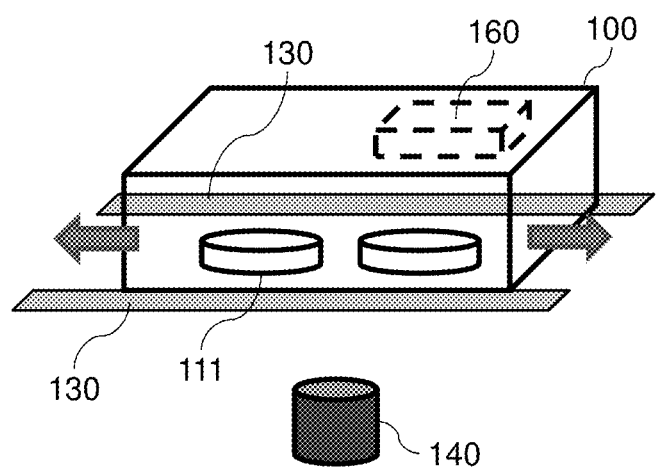
FIG. 3 is a configuration view of the cell culture device 100 according to Embodiment 2.

FIG. 3 is a configuration view of the cell culture device 100 according to Embodiment 2 of the present disclosure. In Embodiment 2, the imaging unit 140 captures images of cells from outside of the cell culture device 100. Thus, at least a portion of the plate 110 on which the culture dish 111 is adapted to be placed is formed optically transparent. Similarly, at least a portion of the bottom of the housing of the cell culture device 100 on which the culture dish 111 is adapted to be placed is formed optically transparent. The plate 110 and the bottom of the housing may also be formed integrally.

In Embodiment 2, the cooling mechanism 120 may be disposed outside of the cell culture device 100. In such a case, for example, a lateral portion of the housing of the cell culture device 100 is formed open or is configured to be freely openable (e.g., with a door attached thereto), so that cells on the culture dish 111 can be cooled.

The configuration of Embodiment 2 is advantageous in that the body of the cell culture device 100 can be made compact as there is no need to dispose the cooling mechanism 120 inside the cell culture device 100. Further, since images of the cells are captured from outside of the cell culture device 100, the light 150 is not necessarily required, and lighting provided in the environment (for example, in the room) in which the cell culture device 100 is disposed can be utilized. Thus, the cell culture device 100 can be made further compact. In addition, since the imaging unit 140 is not disposed in the environment of the cell culture device 100 with a relative humidity of 100%, which is a typical cultivation environment, condensation can be advantageously prevented. It is also possible to dispose a glass heater(s) as a heat source(s) on the upper face, the lower face, or both to prevent condensation. Further, it is also possible to provide a mechanism of controlling the temperature of the heater(s) on the upper face, the lower face, or both by providing feedback about the temperature inside the cell culture device 100.

Regarding Variations of the Present Disclosure

The present disclosure is not limited to the aforementioned embodiments, and includes a variety of variations. For example, although the aforementioned embodiments have been described in detail to clearly illustrate the present disclosure, the present disclosure need not include all of the configurations described in the embodiments. It is possible to replace a part of a configuration of an embodiment with a configuration of another embodiment. In addition, it is also possible to add, to a configuration of an embodiment, a configuration of another embodiment. Further, it is also possible to, for a part of a configuration of each embodiment, add, remove, or substitute a configuration of another embodiment.

In the aforementioned embodiments, the controller 160 determines if detachment of cells has started by analyzing cell images. Instead or in combination, a user may view the cell images and determine if detachment of the cells has started, and if so, determine that the cooling mechanism 120 and the shaking mechanism 130 should be started. The user may then instruct the controller 160 to operate the cooling mechanism 120 and the shaking mechanism 130 based on the determination. The instruction from the user may be input to the controller 160 via an appropriate interface.

The aforementioned embodiments have described that when detachment of cells from the culture dish 111 has started at an unintended timing, the cooling mechanism 120 and the shaking mechanism 130 are operated to suppress formation of undesired adhesion between the cells. In addition, the cooling mechanism 120 and the shaking mechanism 130 can also be used for an ordinary cell detachment step. For example, an ordinary cell detachment step may be performed by operating the cooling mechanism 120 and the shaking mechanism 130 after a predetermined cultivation period has elapsed from the start of cultivation of the cells.

As the cooling mechanism 120, a mechanism of blowing cold air to the cells, or a device (e.g., a Peltier device) disposed in contact with the plate 110 or the culture dish 111 to cool it may be used. Alternatively, other appropriate cooling devices may be used.

The controller 160 may be configured using hardware, such as a circuit device that implements the function of the controller 160, or may also be configured through execution of software, which implements the function of the controller 160, with an arithmetic unit, such as a CPU (Central Processing Unit).

REFERENCE SIGNS LIST

100 Cell culture device
110 Plate
111 Culture dish
120 Cooling mechanism
130 Shaking mechanism
140 Imaging unit
150 Light
160 Controller

The invention claimed is:

1. A cell culture device for culturing cells, comprising:
   a plate adapted to have placed thereon a culture dish for holding cells;
   a cooling mechanism that cools the cells held by the culture dish;
   a shaking mechanism that shakes the culture dish or the plate;
   an imaging unit that captures an image of the cells held by the culture dish; and
   a controller that operates the cooling mechanism and the shaking mechanism,
   wherein the controller operates the cooling mechanism and the shaking mechanism according to a result of determination of whether to operate the cooling mechanism and the shaking mechanism based on the image of the cells captured by the imaging unit,
   wherein the controller determines if at least a part of the cells has been detached from the culture dish by analyzing shapes of the cells based on the image, and
   wherein the controller, upon determining that at least a part of the cells has been detached from the culture dish, operates the cooling mechanism and the shaking mechanism.

2. The cell culture device according to claim 1, wherein the controller shakes the cells by the shaking mechanism while cooling the cells by the cooling mechanism.

3. The cell culture device according to claim 1, wherein the controller receives an input of an instruction to operate the cooling mechanism and the shaking mechanism, and operates the cooling mechanism and the shaking mechanism in response to the received instruction.

4. The cell culture device according to claim 1, wherein the cooling mechanism cools the cells down to a temperature lower than a culture temperature for the cells.

5. The cell culture device according to claim 4,
   wherein:
   the culture dish is configured such that an adhesiveness of the culture dish to the cells changes when a temperature of the culture dish has dropped to a temperature lower than or equal to a threshold temperature, and
   the threshold temperature is lower than or equal to the culture temperature.

6. The cell culture device according to claim 1, further comprising:
   a housing that houses the plate and the imaging unit; and
   a light that illuminates the culture dish placed on the plate.

7. The cell culture device according to claim 1, further comprising a housing that houses the plate,
   wherein:
   the imaging unit is disposed outside of the housing, and
   a portion of the housing located between the plate and the imaging unit is formed optically transparent.

* * * * *